United States Patent [19]

Mulzet et al.

[11] 4,174,637
[45] Nov. 20, 1979

[54] PRESSURE MONITORING SYSTEM

[75] Inventors: Alfred P. Mulzet, Endicott; Gary A. Trudgen, Endwell, both of N.Y.

[73] Assignee: International Business Machines Corporation, Armonk, N.Y.

[21] Appl. No.: 952,766

[22] Filed: Oct. 19, 1978

[51] Int. Cl.² .............................................. G01L 7/02
[52] U.S. Cl. .................. 73/730; 73/119 A; 128/DIG. 3
[58] Field of Search ............ 73/730, 119 A, 115; 128/2.05 E, DIG. 3, 214 E, 214 F, DIG. 12, DIG. 13

[56] References Cited

U.S. PATENT DOCUMENTS

| 3,240,207 | 3/1966 | Barker et al. | 73/730 |
| 3,866,473 | 2/1975 | Teitelbaum et al. | 73/730 |
| 3,937,087 | 2/1976 | Heggie | 73/730 |

Primary Examiner—Donald O. Woodiel
Attorney, Agent, or Firm—Paul M. Brannen

[57] ABSTRACT

A pressure monitoring system especially suitable for use with extra-corporeal circulation systems such as dialyzers, blood cell separators, oxygenators and the like, in which the internal system pressure must be monitored at one or more locations in the blood circuit, and appropriate warnings provided of pressure increases or decreases within defined limits. An initial pressure measuring cycle is provided and must be completed successfully before the main operating cycle of the overall system can begin. A pressure transducer provides signals to a digital closed-loop system which provides a suitable compensation during the initial or primary cycle and then holds that compensation value during the machine running cycle. Excursions of pressure beyond upper and lower limits of the stored reference or compensation value, in either direction, will cause the running cycle to terminate automatically.

8 Claims, 3 Drawing Figures

PRESSURE MONITORING SYSTEM

BACKGROUND OF THE INVENTION (1) Field of the Invention

This invention relates to pressure monitoring systems, and particularly to a pressure monitoring system utilizing electrical signals which are analog representations of the pressures to be measured. More particularly, the invention relates to a pressure monitoring system in which an initialization procedure checks the proper response of the system.

(2) Description of the Prior Art

Pressure transducers employing strain gauges connected to bridge circuits are known in the art, as disclosed in U.S. Pat. Nos. 3,535,937 and 3,866,473, for example. Also, U.S. Pat. No. 3,946,731 proposes the control of an extracorporeal circulation system by at least one pressure sensor. However, none of the prior art teaches a system of the type herein disclosed, in which a pressure sensing system is checked for proper response during an initialization mode, to provide greater assurance of correct operation during the actual running cycle of the overall system. Nor does the prior art teach a system for pressure monitoring using a closedloop digital control of a reference signal determined during an initialization cycle.

SUMMARY OF THE INVENTION

It is accordingly a principal object of the present invention to provide an improved pressure monitoring system.

Another object of the invention is to provide an improved pressure monitoring system for extracorporeal circulation systems.

A further object of the invention is to provide a pressure monitoring system in which a reference signal is generated during an initialization cycle and is used to set signal limits for a subsequent operating cycle.

Yet another object of the invention is to provide an improved pressure monitoring system utilizing a closedloop digital control for generating a reference signal.

Briefly described, the present invention comprises a pressure transducer arranged to be influenced by the internal pressure in a section of flexible tubing contained in a U-shaped channel in a pressure block. During an initial or priming cycle of the extracorporeal circulatory system with which the pressure monitor system is associated, the flexible wall tubing or line is placed within the pressure sensing block. With the line properly inserted, the block is designed to exert a certain pre-load pressure within a certain range on the transducer. A properly inserted fluid line is required to obtain accurate relative pressure measurements during the subsequent run cycle.

The pressure amplifier has the capacity to compensate of "zero out" the transducer pre-load signal. The amplifier compensation range is tightly held to within the desired pre-load range. Thus if the pre-load transducer signal and hence, the pressure is not within the expected range because of improper fluid line insertion, the amplifier will not be able to zero out the pre-load signal. When this occurs, an amplifier output line goes positive and prevents the operation of the circulatory system. The machine operator must then reinsert the fluid line and restart the prime cycle.

After the machine has successfully completed its priming cycle and goes into a run cycle, the amplifier compensation ability is disabled by a signal received from the principal controller of the overall system, and the amplifier thereafter functions as a relative pressure change detector, detecting pressure decreases or increases within defined limits. If such changes occur, the principal system is immediately shut down and suitable alarms actuated.

The foregoing and other objects, features and advantages of the invention will be apparent from the following more particular description of a preferred embodiment of the invention, as illustrated in the accompanying drawings.

DETAILED DESCRIPTION OF A PREFERRED EMBODIMENT

Figure 1:
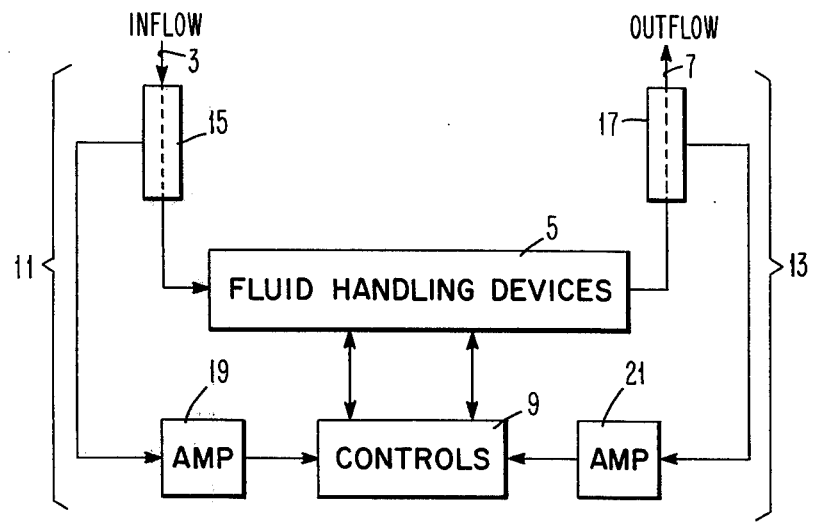
FIG. 1 is a highly schematic block diagram of an extracorporeal circulation system in which the pressure monitoring system in accordance with the present invention may be used.

Referring to FIG. 1 of the drawings, there is shown in highly schematic form a block diagram of an extracorporeal circulation system in which the present invention may be utilized. The fluid path or circuit extends from an inflow line designated by reference character 3 through various fluid handling devices 5, which depend upon the nature of the system, but would include pumping devices, control valves, treatment devices such as dialyzers or centrifuges, warming devices, bubble detectors and the like. From the fluid handling devices 5 an outflow line 7 provides a return path such as to a patient undergoing in vivo treatment. The apparatus is governed by suitable controls indicated by the block 9.

In systems of the type shown in FIG. 1, it is essential to provide pressure monitoring at various points in the overall system. In the illustrative arrangement shown in FIG. 1, pressure monitors 11 and 13 are to be used to monitor the pressure on the inflow line 3 and the outflow lines 7, respectively. Each of the pressure monitors consists of a pressure monitoring block indicated at 15 and 17, through which the associated tubing 3 and 7 pass, and which contain a suitable pressure transducer which supplies electrical output signals to an associated amplifier system 19 and 21. The outputs from the amplifier systems 19 and 21 are supplied to the control system 9, to provide appropriate controls and alarms if and when the pressures in the lines 3 and 7 depart from preset limits.

Figure 2:
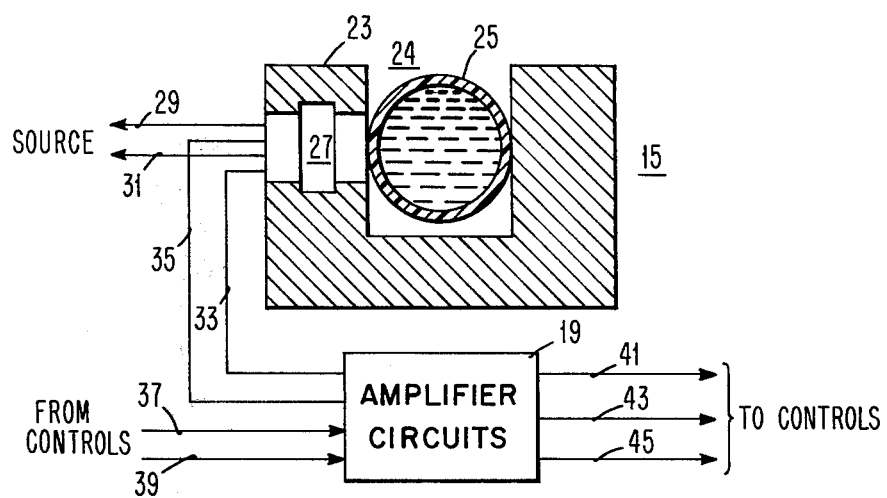
FIG. 2 is a schematic diagram illustrating the basic relationship between the tubing, pressure block, transducer and amplifier.

The arrangement of the pressure monitoring apparatus is shown in further detail in FIG. 2. Each of the pressure monitoring sensing blocks 15, 17 include a block 23 having a channel 24 therein in which the appropriate tubing or fluid line 25 is inserted, as can be seen from the cross-sectional view in FIG. 2. Since the tubing such as 3 and 7 usually form part of a disposable set, a new set of tubing must be inserted in the pressure sensors for each use of the complete system. A principal function of the present invention is to provide means for determining that the tubing 25 has been properly inserted in block 23. In one of the sidewalls of block 23 opening on the channel 24, there is mounted a pressure transducer 27. The details of this device are not shown, but they are well-known in the art and are commercially available transducers utilizing resistance type strain gauges arranged in a bridge circuit configuration. In accordance with the usual practice with respect to strain gauge bridge circuits, a source of electrical energy is connected to the bridge over the lines 29 and 31. Output signals are developed across a second set of lines 33 and 35, and are supplied as inputs to the amplifier circuits 19. Additional control circuits are provided from the controls 9 over lines 37 and 39, and outputs from the amplifier circuits are provided to the controls 9 by lines 41, 43 and 45.

With the fluid line 25 properly inserted into block 23, the parts are proportioned and arranged so that the tubing will exert a certain pre-load pressure, for example, from 3 pounds per square inch to 9 pounds per square inch on the pressure transducer 27. If the line is improperly inserted, of course, the proper preload pressure will not be obtained.

The amplifier circuits 19 have the ability to compensate or zero out the transducer pre-load signal. The amplifier compensation range is tightly held to within the desired pre-load range, for example, 3 psi to 9 psi. Thus, if the pressure transducer pre-load is not within the expected pre-load range because of improper insertion of tubing 25 into channel 24 of block 23, the amplifier will not be able to zero out the signal provided under the pre-load conditions.

When this occurs, the amplifier signal output line 45 will go positive and prevent the system of FIG. 1 from going into the main operating cycle or run mode. A suitable alarm can notify the operator that the tubing must be reinserted and the priming cycle restarted.

Once the fluid line is properly inserted in channel 24, and the machine goes into its run cycle, the amplifier circuits 19 compensation capability is disabled by a signal on the input to the amplifier circuits 19 on line 39. The amplifier circuits 19 now function as a relative pressure change detector, capable of sensing a pressure decrease of 2.25 psi or a pressure increase of 5.25 psi, for example. If either of the preceding pressure changes occur, the machine running cycle will be terminated until the cause of the pressure change is corrected. These pressure decrease signals and pressure increase signals when they exist, are supplied to the control circuits via the output lines 41 and 43 from amplifier circuits 19. The remaining input signal line to the amplifier circuits 19 is line 37, which carries clock or gating signals generated within the controls 9 of the system of FIG. 1.

Figure 3:
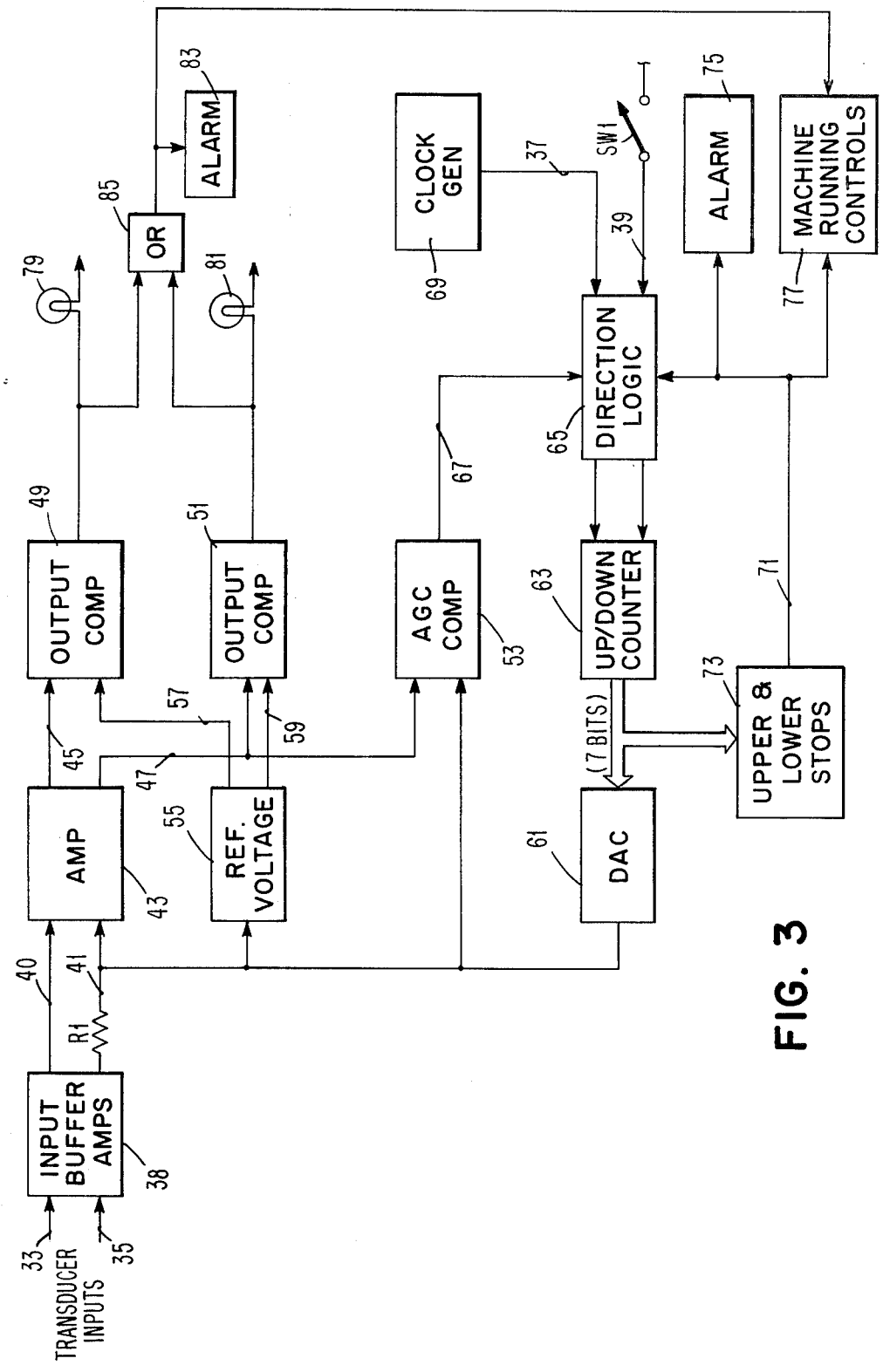
FIG. 3 is a detailed schematic block diagram of the amplifier portion of the pressure monitoring system. Similar reference characters refer to similar parts in each of the several views.

Referring to FIG. 3 of the drawings, the circuitry found in the amplifier circuits 19 is shown in block diagram form. The transducer signal lines 33 and 35 which carry the differential signal from the transducer 27 are connected to the input of suitable input buffer amplifiers 38. The exact structure of these buffer amplifiers is not shown since it is not germane to the invention and any one of a number of well-known configurations could be employed. This is also true of the remaining components of the circuitry of FIG. 3, in which each of the blocks designates a circuit which is well-known in the art and may take any one of a number of various forms depending upon the choice of the designer.

The output of the input buffer amplifiers 38 comprises a signal line 40 and a reference line 41 which is connected with a series resistor R1, as shown. The buffer amplifiers are provided so that the remainder of the circuitry is not sensitive to the impedance tolerances of the pressure transducer.

Lines 40 and 41 are connected to the inputs of amplifier 43, the outputs of which are supplied to a number of circuits via the output lines 45 and 47. Line 45 is connected to the input of an output comparator circuit 49, and line 47 is connected to the input of an output comparator 51, as well as to one input of an automatic gain control comparator 53.

The reference line 41 is also connected to the input of a reference voltage generator 55, the outputs of which are connected to comparators 49 and 51 by the output lines 57 and 59. Line 41 is also connected as one of the two inputs to the automatic gain control comparator 53.

The signal on reference line 41 is an analog signal constituting the output of a digital-to-analog converter 61, which has a 7 bit digital input thereto, comprising the output of a digital up/down counter 63.

The up/down counter 63 is governed by pulses supplied via a set of combinatorial circuits designated as the direction logic, reference character 65. The direction logic 65 provides pulses which cause counter 63 to count either up or down depending on the presence or absence of signals at the input of the logic 65. These inputs comprise a signal line 67 carrying the output of the automatic gain control comparator 53, a clock signal line 37 which supplies clocking pulses generated by a clock generator 69 located in the control unit 9, a control signal line 39 governed by a switch SW1 in the control unit 9, which is closed when the machine goes into the run mode, and an internal connection 71 which is the output of the upper and lower stop circuits 73. The line 71 also is supplied to a suitable alarm device 75 and to the machine running controls 77 so that a signal on the line 71 will not only operate the alarm 75 to alert the operator, but will also shut down the machine running cycle. The upper and lower stops 73 constitute combinatorial decoding logic which provides outputs on line 71 when the up/down counter exceeds predetermined counts in the output thereof.

The outputs of comparators 49 and 51 are supplied to individual indicators 79 and 81 and to a common alarm device 83. These indicators and associated alarm will indicate to the operator, during the running cycle, whether the pressure in the tubing has decreased by 2.25 psi or has increased over 5.25 psi.

These signals from comparators 49 and 51 are supplied to the alarm 83 via an OR circuit 85, which also supplies a signal to the machine running controls to halt the running cycle of the machine, if the pressure goes beyond the desired limits.

In operation, the machine operator will insert the appropriate tubing sections into the pressure sensing blocks prior to starting of the total system. When the system is placed in its priming cycle, the pressure monitors sense the pressure in the fluid lines and if the output falls within the proper pressure limits, say, for example, 3 psi to 9 psi then the machine can proceed to the run cycle. During the running cycle, if the pressure limits are exceeded in either direction, indicator lamp 79 or 81 will be lighted and an alarm provided by alarm 83 as well as a signal to the machine running control 77 to stop the operation of the extracorporeal circulation system.

When the machine is in its run cycle, the amplifier compensation capability is disabled as a result of operation of switch SW1, which disables the direction logic 65. The amplifier system now functions as a relative pressure change detector capable of sensing a pressure decrease 2.25 psi or pressure increase of 5.25 psi. If either of these pressure changes occur, the machine running cycle will be terminated. Thus, it is apparent that the present invention provides a pressure monitoring system which is arranged so that the system must be in condition to operate properly before the apparatus associated therewith can be placed within its full operating condition.

While the invention has been particularly shown and described with reference to a preferred embodiment thereof, it will be understood by those skilled in the art that various changes in form and details may be made therein without departing from the spirit and scope of the invention.

I claim:

1. A pressure monitoring system for determining the pressure of fluid in a section of flexible wall tubing comprising, in combination, a supporting block having a channel therein in which a section of fluid filled tubing is inserted, a pressure transducer mounted in said block, having a predetermined initial load imposed thereon by the fluid-filled tubing inserted in said block, and providing a first electrical signal having a value dependent upon the value of said initial load, a reference signal source, comparing means connected to said transducer and said reference signal source for comparing the signal from said transducer with the reference signal, reference signal control means connected to said comparing means and said reference signal source for varying said reference signal in accordance with the variation in the output of said comparing means, and indicating means for indicating variations in said reference signal.

2. A pressure monitoring system as claimed in claim 1, further including alarm means governed by said comparing means for providing an alarm when said comparing means provides an output indicating a variation of said reference signals exceeding predetermined limits.

3. A pressure monitoring system for determining the pressure of fluid in a section of flexible wall tubing, comprising, in combination, a pressure block having a channel therein for receiving a section of said tubing, a pressure transducer mounted in a wall of said channel for contact with the wall of said tubing, and providing a transducer signal proportional to the pressure in said tubing, amplifier means connected to said transducer for amplifying the transducer output signal, a reference voltage source, first and second comparing means connected to the output of said amplifier means and to said reference voltage source to provide first and second comparison output signals when the pressure in said tubing increases or decreases within predetermined limits, a reference signal line connected to one input of said amplifier means to govern the output signal therefrom, an automatic gain control loop for varying the signal on said reference signal line in accordance with variations in one output signal from said amplifier means and, means for indicating excursions of said automatic gain control loop beyond predetermined limits.

4. A pressure monitoring system as claimed in claim 3, in which said automatic gain control loop comprises a digital closed-loop system including a source of clock pulses, an up/down counter, digital logic control circuits connected to said counter and said source for supplying pulses to said counter in accordance with the output signal from said amplifier means and said reference voltage, and a digital-to-analog connector connected to the output of said counter and said reference signal line for varying the signal on said reference line in accordance with the digital output of said counter.

5. A pressure monitoring system as claimed in claim 4, further including logic means connected to the output of said counter and responsive to counter outputs exceeding predetermined upper and lower limits for operating said indicating means.

6. A pressure monitoring system as claimed in claim 5, further including inhibiting means for disabling said logic means to thereby halt the supply of clock pulses to said counter.

7. A pressure monitoring system as claimed in claim 6, in which said inhibiting means comprises logic means connected to said counter for decoding upper and lower counter outputs, either of which will cause said logic means to disable the supply of pulses to the counter.

8. A pressure monitoring system as claimed in claim 6, in which control switch means is additionally provided to govern said inhibiting means.

* * * * *